(12) United States Patent
Kahn et al.

(10) Patent No.: US 10,485,474 B2
(45) Date of Patent: Nov. 26, 2019

(54) SLEEP MONITORING SYSTEM

(71) Applicants: Philippe Richard Kahn, Santa Cruz, CA (US); Arthur Kinsolving, Santa Cruz, CA (US)

(72) Inventors: Philippe Richard Kahn, Santa Cruz, CA (US); Arthur Kinsolving, Santa Cruz, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 0 days.

(21) Appl. No.: 14/949,880

(22) Filed: Nov. 23, 2015

(65) Prior Publication Data

US 2016/0073951 A1  Mar. 17, 2016

Related U.S. Application Data

(63) Continuation of application No. 13/545,963, filed on Jul. 10, 2012, now Pat. No. 9,192,326.

(60) Provisional application No. 61/507,567, filed on Jul. 13, 2011.

(51) Int. Cl.
| | |
|---|---|
| A61B 5/00 | (2006.01) |
| A61B 5/11 | (2006.01) |
| G04G 13/02 | (2006.01) |
| G04G 21/04 | (2013.01) |

(Continued)

(52) U.S. Cl.
CPC .......... *A61B 5/4812* (2013.01); *A61B 5/1118* (2013.01); *A61B 5/4806* (2013.01); *A61B 5/681* (2013.01); *A61B 5/7275* (2013.01); *A61B 5/746* (2013.01); *A61M 21/00* (2013.01); *G04G 13/026* (2013.01); *G04G 21/04* (2013.01); *A61B 5/4809* (2013.01); *A61B 5/7475* (2013.01);

(Continued)

(58) Field of Classification Search
CPC .... G04G 13/026; G04G 21/04; A61B 5/1118; A61B 5/4806; A61B 5/746; A61B 5/7475; A61B 5/681; A61B 2562/0219
USPC ......... 600/300–301, 587, 595; 340/500, 540, 340/573.1, 573.7, 575
See application file for complete search history.

(56) References Cited

U.S. PATENT DOCUMENTS

| | | |
|---|---|---|
| 3,798,889 A | 3/1974 | Chadwick |
| 4,228,806 A | 10/1980 | Lidow |
| 4,297,685 A | 10/1981 | Brainard, II |

(Continued)

FOREIGN PATENT DOCUMENTS

| | | |
|---|---|---|
| AU | 2003203967 | 11/2004 |
| DE | 19642316 A1 | 4/1998 |

(Continued)

OTHER PUBLICATIONS

"Fitbit Product Manual," <http://www.fitbit.com/manual>, Last updated Mar. 29, 2010, 20 pages.

(Continued)

*Primary Examiner* — Rene T Towa
(74) *Attorney, Agent, or Firm* — HIPLegal LLP; Judith Szepesi

(57) ABSTRACT

A method comprising monitoring a user's movements and determining when the user is falling asleep into a sleep session. The method further comprising identifying the sleep session as a power nap or a longer sleep, and waking up the (Continued)

user at a predetermined time, based on a combination of user preferences and measured information regarding the sleep session.

17 Claims, 18 Drawing Sheets

(51) Int. Cl.
    *A61M 21/00*      (2006.01)
    *G16H 40/63*      (2018.01)

(52) U.S. Cl.
    CPC ............... *A61B 2562/0219* (2013.01); *A61M 2021/0083* (2013.01); *G16H 40/63* (2018.01)

(56) References Cited

U.S. PATENT DOCUMENTS

| | | | |
|---|---|---|---|
| 4,573,804 | A | 3/1986 | Kavoussi et al. |
| 4,858,609 | A | 8/1989 | Cole |
| 5,008,865 | A | 4/1991 | Shaffer et al. |
| 5,335,657 | A | 8/1994 | Terry, Jr. et al. |
| 5,458,105 | A | 10/1995 | Taylor et al. |
| 5,545,192 | A | 8/1996 | Czeisler et al. |
| 5,928,133 | A | 7/1999 | Halyak |
| 6,239,706 | B1 | 5/2001 | Yoshiike et al. |
| 6,350,275 | B1 | 2/2002 | Vreman et al. |
| 6,361,508 | B1 | 3/2002 | Johnson et al. |
| 6,468,234 | B1 | 10/2002 | Van der Loos et al. |
| 6,547,728 | B1 | 4/2003 | Cornuejols |
| 6,556,222 | B1 | 4/2003 | Narayanaswami |
| 6,834,436 | B2 | 12/2004 | Townsend et al. |
| 6,888,779 | B2 | 5/2005 | Mollicone et al. |
| 6,928,031 | B1 | 8/2005 | Kanevsky et al. |
| 6,963,271 | B1 | 11/2005 | Fyffe |
| 7,106,662 | B1 | 9/2006 | Acker |
| 7,280,439 | B1 | 10/2007 | Shaddox |
| 7,366,572 | B2 | 4/2008 | Heruth et al. |
| 7,572,225 | B2 | 8/2009 | Stahmann et al. |
| 7,914,468 | B2 | 3/2011 | Shalon et al. |
| 8,179,270 | B2* | 5/2012 | Rai ..................... A61B 5/048 340/575 |
| 8,398,546 | B2 | 3/2013 | Pacione et al. |
| 8,475,339 | B2 | 7/2013 | Hwang et al. |
| 8,680,974 | B2 | 3/2014 | Meiertoberens et al. |
| 8,738,925 | B1 | 5/2014 | Park et al. |
| 8,892,036 | B1 | 11/2014 | Causey et al. |
| 8,942,719 | B1 | 1/2015 | Hyde et al. |
| 9,474,876 | B1 | 10/2016 | Kahn et al. |
| 9,594,354 | B1 | 3/2017 | Kahn et al. |
| 2002/0080035 | A1 | 6/2002 | Youdenko |
| 2003/0095476 | A1 | 5/2003 | Mollicone et al. |
| 2003/0204412 | A1 | 10/2003 | Brier |
| 2003/0231495 | A1 | 12/2003 | Searfoss |
| 2004/0034289 | A1 | 2/2004 | Teller et al. |
| 2004/0049132 | A1 | 3/2004 | Barron et al. |
| 2004/0133081 | A1 | 7/2004 | Teller et al. |
| 2004/0210155 | A1 | 10/2004 | Takemura et al. |
| 2004/0218472 | A1 | 11/2004 | Narayanaswami et al. |
| 2005/0012622 | A1 | 1/2005 | Sutton |
| 2005/0075116 | A1 | 4/2005 | Laird et al. |
| 2005/0143617 | A1 | 6/2005 | Auphan |
| 2005/0154330 | A1* | 7/2005 | Loree, IV ............. A61B 5/103 600/595 |
| 2005/0190065 | A1 | 9/2005 | Ronnholm |
| 2005/0237479 | A1 | 10/2005 | Rose |
| 2005/0245793 | A1 | 11/2005 | Hilton et al. |
| 2005/0288904 | A1 | 12/2005 | Warrior et al. |
| 2006/0025299 | A1 | 2/2006 | Miller et al. |
| 2006/0064037 | A1 | 3/2006 | Shalon et al. |
| 2006/0097884 | A1 | 5/2006 | Jang et al. |
| 2006/0150734 | A1 | 7/2006 | Mimnagh-Kelleher et al. |
| 2006/0252999 | A1 | 11/2006 | DeVaul et al. |
| 2006/0266356 | A1 | 11/2006 | Solos et al. |
| 2006/0279428 | A1 | 12/2006 | Sato et al. |
| 2006/0293602 | A1 | 12/2006 | Clark |
| 2006/0293608 | A1 | 12/2006 | Rothman et al. |
| 2007/0016091 | A1 | 1/2007 | Butt et al. |
| 2007/0016095 | A1 | 1/2007 | Low et al. |
| 2007/0191692 | A1 | 8/2007 | Hsu et al. |
| 2007/0251997 | A1 | 11/2007 | Brown et al. |
| 2007/0287930 | A1 | 12/2007 | Sutton |
| 2008/0062818 | A1 | 3/2008 | Plancon et al. |
| 2008/0125820 | A1 | 5/2008 | Stahmann et al. |
| 2008/0191885 | A1 | 8/2008 | Loree, IV et al. |
| 2008/0234785 | A1* | 9/2008 | Nakayama ........... A61B 5/0205 607/62 |
| 2009/0030767 | A1 | 1/2009 | Morris et al. |
| 2009/0048540 | A1 | 2/2009 | Otto et al. |
| 2009/0069644 | A1 | 3/2009 | Hsu et al. |
| 2009/0082699 | A1 | 3/2009 | Bang et al. |
| 2009/0105785 | A1 | 4/2009 | Wei et al. |
| 2009/0121826 | A1 | 5/2009 | Song et al. |
| 2009/0128487 | A1 | 5/2009 | Langereis et al. |
| 2009/0143636 | A1 | 6/2009 | Mullen et al. |
| 2009/0177327 | A1 | 7/2009 | Turner et al. |
| 2009/0203970 | A1 | 8/2009 | Fukushima et al. |
| 2009/0207028 | A1 | 8/2009 | Kubey et al. |
| 2009/0227888 | A1 | 9/2009 | Salmi et al. |
| 2009/0264789 | A1 | 10/2009 | Molnar et al. |
| 2010/0010330 | A1 | 1/2010 | Rankers et al. |
| 2010/0061596 | A1 | 3/2010 | Mostafavi et al. |
| 2010/0075807 | A1 | 3/2010 | Hwang et al. |
| 2010/0079291 | A1 | 4/2010 | Kroll et al. |
| 2010/0079294 | A1 | 4/2010 | Rai et al. |
| 2010/0083968 | A1 | 4/2010 | Wondka et al. |
| 2010/0100004 | A1 | 4/2010 | van Someren |
| 2010/0102971 | A1 | 4/2010 | Virtanen et al. |
| 2010/0152543 | A1 | 6/2010 | Heneghan et al. |
| 2010/0152546 | A1 | 6/2010 | Behan et al. |
| 2010/0256512 | A1 | 10/2010 | Sullivan |
| 2010/0331145 | A1 | 12/2010 | Lakovic et al. |
| 2011/0015467 | A1 | 1/2011 | Dothie et al. |
| 2011/0015495 | A1 | 1/2011 | Dothie et al. |
| 2011/0018720 | A1 | 1/2011 | Rai et al. |
| 2011/0058456 | A1 | 3/2011 | De et al. |
| 2011/0137836 | A1 | 6/2011 | Kuriyama et al. |
| 2011/0160619 | A1 | 6/2011 | Gabara |
| 2011/0190594 | A1 | 8/2011 | Heit et al. |
| 2011/0199218 | A1 | 8/2011 | Caldwell et al. |
| 2011/0230790 | A1* | 9/2011 | Kozlov ................. A61B 5/4812 600/595 |
| 2011/0295083 | A1 | 12/2011 | Doelling et al. |
| 2012/0083715 | A1 | 4/2012 | Yuen et al. |
| 2012/0232414 | A1 | 9/2012 | Mollicone et al. |
| 2012/0243379 | A1 | 9/2012 | Balli |
| 2012/0253220 | A1 | 10/2012 | Rai et al. |
| 2013/0012836 | A1 | 1/2013 | Veiga et al. |
| 2013/0018284 | A1 | 1/2013 | Kahn et al. |
| 2013/0023214 | A1 | 1/2013 | Wang et al. |
| 2013/0053653 | A1 | 2/2013 | Cuddihy et al. |
| 2013/0053656 | A1 | 2/2013 | Mollicone et al. |
| 2013/0060306 | A1 | 3/2013 | Colbauch |
| 2013/0144190 | A1 | 6/2013 | Bruce et al. |
| 2013/0208576 | A1 | 8/2013 | Loree et al. |
| 2013/0286793 | A1 | 10/2013 | Umamoto |
| 2013/0289419 | A1 | 10/2013 | Berezhnyy et al. |
| 2013/0310658 | A1 | 11/2013 | Ricks et al. |
| 2014/0005502 | A1 | 1/2014 | Klap et al. |
| 2014/0051938 | A1 | 2/2014 | Goldstein et al. |
| 2014/0085077 | A1 | 3/2014 | Luna et al. |
| 2014/0135955 | A1 | 5/2014 | Burroughs |
| 2014/0200691 | A1 | 7/2014 | Lee et al. |
| 2014/0207292 | A1 | 7/2014 | Ramagem et al. |
| 2014/0219064 | A1 | 8/2014 | Filipi et al. |
| 2014/0232558 | A1 | 8/2014 | Park et al. |
| 2014/0256227 | A1 | 9/2014 | Aoki et al. |
| 2014/0259417 | A1 | 9/2014 | Nunn et al. |
| 2014/0276227 | A1 | 9/2014 | Perez |
| 2014/0288878 | A1 | 9/2014 | Donaldson |
| 2014/0371635 | A1 | 12/2014 | Shinar et al. |
| 2015/0068069 | A1 | 3/2015 | Tran et al. |
| 2015/0073283 | A1 | 3/2015 | Vugt et al. |
| 2015/0098309 | A1 | 4/2015 | Adams et al. |

(56) References Cited

U.S. PATENT DOCUMENTS

| | | |
|---|---|---|
| 2015/0141852 A1 | 5/2015 | Dusanter et al. |
| 2015/0148871 A1 | 5/2015 | Maxik et al. |
| 2015/0173671 A1 | 6/2015 | Paalasmaa et al. |
| 2015/0178362 A1 | 6/2015 | Wheeler |
| 2015/0190086 A1 | 7/2015 | Chan et al. |
| 2015/0233598 A1 | 8/2015 | Shikii et al. |
| 2015/0265903 A1 | 9/2015 | Kolen et al. |
| 2017/0003666 A1 | 1/2017 | Nunn et al. |

FOREIGN PATENT DOCUMENTS

| | | |
|---|---|---|
| EP | 1139187 B1 | 10/2010 |
| JP | 8160172 | 6/1996 |
| JP | 2007132581 A | 5/2007 |
| KR | 1020009085403 | 6/2011 |
| KR | 1020100022217 | 3/2012 |
| WO | 9302731 | 2/1993 |
| WO | 2008038288 A3 | 5/2009 |
| WO | 2009099292 A2 | 8/2009 |
| WO | 2011141840 A1 | 11/2011 |

OTHER PUBLICATIONS

"How BodyMedia Fit Works", <http://www.bodymedia.com/Shop/Learn-More/How-it-works>, accessed Jun. 17, 2011, 2 pages.

"Power Nap," <en.wikipedia.org/wiki/Powersub.—nap>, Last Modified Sep. 20, 2012, 4 pages.

"Sara Mednick," <en.wikipedia.org/wiki/Sara.sub.—Mednick>, Last Modified Sep. 12, 2012, 2 pages.

"Sleep Debt," <en.wikipedia.org/wiki/Sleep.sub.--debt>, Last Modified Aug. 25, 2012, 3 pages.

"Sleep Inertia," <en.wikipedia.org/wiki/Sleep.sub.--inertia>, Last Modified Sep. 12, 2012, 2 pages.

"Sleep," <en.wikipedia.org/wiki/Sleep.sub.—stages#Physiology>, Last Modified Oct. 5, 2012, 21 pages.

"Slow Wave Sleep," <en.wikipedia.org/wiki/Slow-wave.sub.—sleep>, Last Modified Jul. 22, 2012, 4 pages.

Actigraphy, From Wikipedia, the free encyclopedia, downloaded at: http://en.wikipedia.org/wiki/Actigraphy on Apr. 24, 2014, 4 pages.

David F. Dinges, <en.wikipedia.org/wiki/David_Dinges>, Last Modified Sep. 12, 2012, 2 pages.

Desai, Rajiv, The Sleep, Archive for Mar. 2011, Dr. Rajiv Desai Blog, Mar. 17, 2011, 46 pages.

Jaines, Kira, "Music to Help You Fall Sleep," <http://www.livestrong.com/article/119802-music-fall-sleep/>, May 10, 2010, 2 pages.

JETLOG Reviewers Guide, <http://wwwjetlog.com/fileadmin/Presse.sub.—us/24x7ReviewersGuide.pdf- >, 2009, 5 pages.

Lichstein, et al., Actigraphy Validation with Insomnia, Sleep, vol. 29, No. 2, 2006, pp. 232-239.

Liden, Craig B, et al, "Characterization and Implications of the Sensors Incorporated into the SenseWear(TM) Armband for Energy Expenditure and Activity Detection", <http://www.bodymedia.com/Professionals/Whitepapers/Characterization-and-Implications-of-the-Sensors-Incorporated-into-the-SenseWear>, accessed Jun. 17, 2011, 7 pages.

Patel, et al., Validation of Basis Science Advanced Sleep Analysis, Estimation of Sleep Stages and Sleep Duration, Basis Science, San Francisco, CA, Jan. 2014, 6 pages.

PCT Application No. PCT/US2012146477, Search History, Date of Search Sep. 12, 2012, 3 pages.

PCT Application No. PCT/US2012/46477, Search History, Date of Search Sep. 12, 2012, 3 pages.

PCT/US2012/046477, International Search Report and Written Opinion, dated Sep. 28, 2012, 10 pages.

PCT/US2013/028939, International Preliminary Report on Patentability, dated Jan. 23, 2014, 8 pages.

Pires, P. D. C. Activity Characterization from Actimetry Sensor Data for Sleep Disorders Diagnosis, Universidade Técnica de Lisboa, Sep. 2008, 60 pages.

Pollak, et al., How Accurately Does Wrist Actigraphy Identify the States of Sleep and Wakefulness?, Actigraphy and Sleep, Sleep, vol. 24, No. 8, 2001, pp. 957-965.

PowerNap iPhone App, <http://forums.precentral.net/webos-apps-software/223091-my-second-app- -powernap-out-app-catalog-nap-timer.html>, Jan. 6, 2010, 10 pages.

Sound-Remedies.com: Sonic Solutions for Health, Learning & Productivity, <http://www.sound-remedies.com/ammusforslee.html>, Accessed May 23, 2013, 2 pages.

Sunseri, Maria, et al, "The SenseWear (TM) Armband as a Sleep Detection Device," <http://sensewear.bodymedia.com/SenseWear-Studies/SW-Whitepapers/The-SenseWear-armband-as-a-Sleep-Detection-Device>, 2005, 9 pages.

* cited by examiner single button user interface: Circular Approach
(button cycles through modes)

single button user interface: Linear Approach
(button cycles through modes)

| Trigger | Examples |
|---|---|
| User Interface | night/day setting, user preferences, button push to initiate power nap |
| Time Based | time since last "overnight" sleep, current time of day |
| Pattern Based | user's statistical pattern |

Fig. 6

SLEEP MONITORING SYSTEM

RELATED APPLICATION

The present application claims priority to U.S. patent application Ser. No. 13/545,963, filed on Jul. 10, 2012, and issued as U.S. Pat. No. 9,192,326 on Nov. 24, 2015, which claims priority to U.S. Provisional Application Ser. No. 61/507,567, filed on Jul. 13, 2011, both of which are incorporated herein by reference.

FIELD

The present invention is related to motion sensing, and more particularly to monitoring a user's motions to improve rest.

BACKGROUND

As accelerometers and other motion sensors are becoming cheaper and smaller. There are numerous systems available, which enable a user to monitor his or her motions, whether in activity or sleep.

For example, there are pedometers or other activity monitors that track a user's activities to improve health. There are also some sleep monitors, which use accelerometers.

BRIEF DESCRIPTION OF THE FIGURES

The present invention is illustrated by way of example, and not by way of limitation, in the figures of the accompanying drawings and in which like reference numerals refer to similar elements and in which:

FIG. 6 is a chart of one embodiment of conditions that may be used to differentiate between types of sleep.

DETAILED DESCRIPTION

Figure 1A:
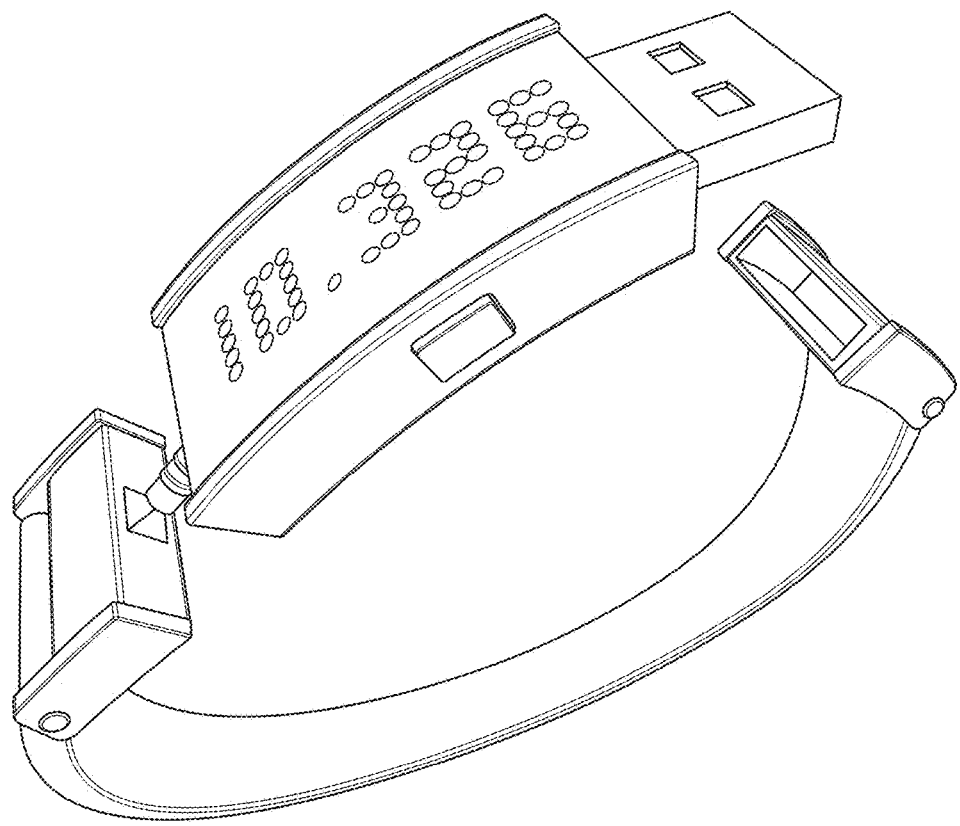
FIGS. 1A-1G are embodiments of the system.
Figure 1B:
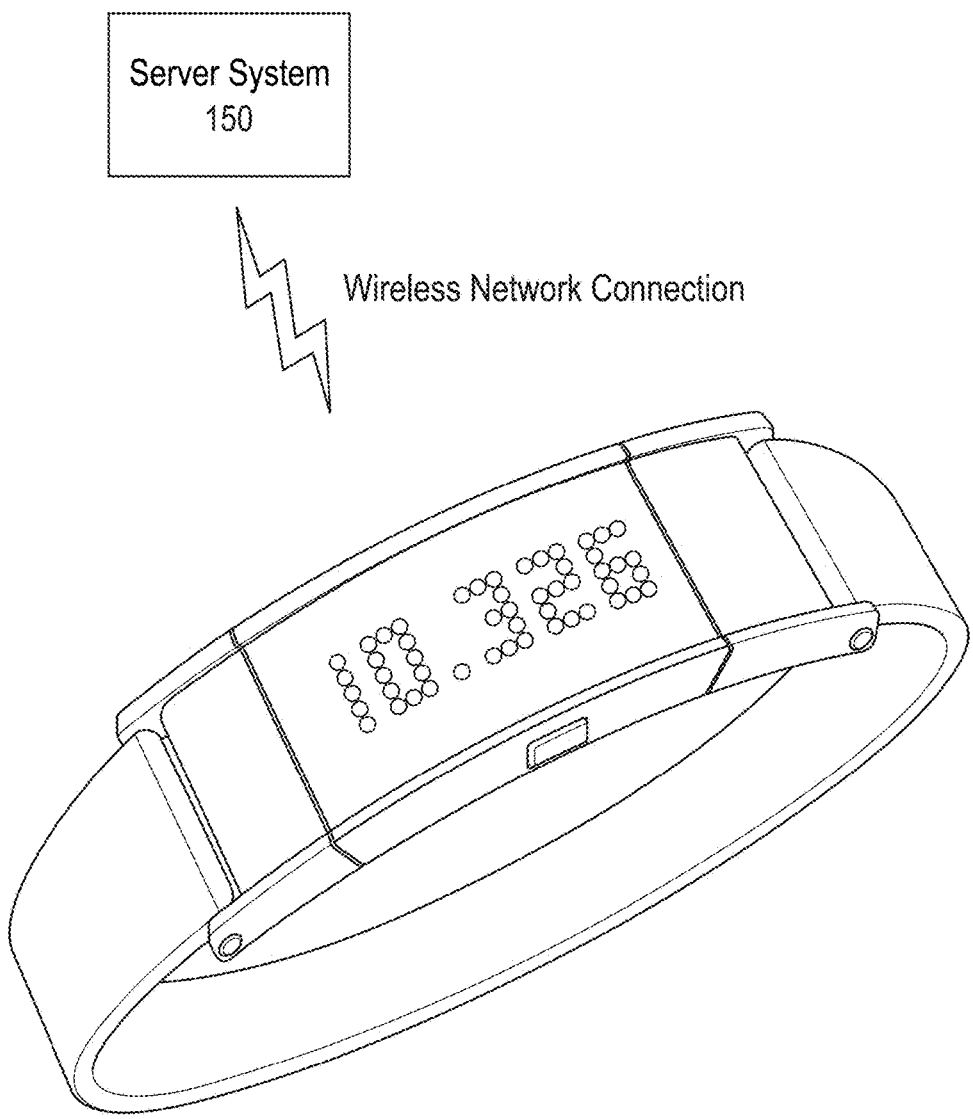
Figure 1C:
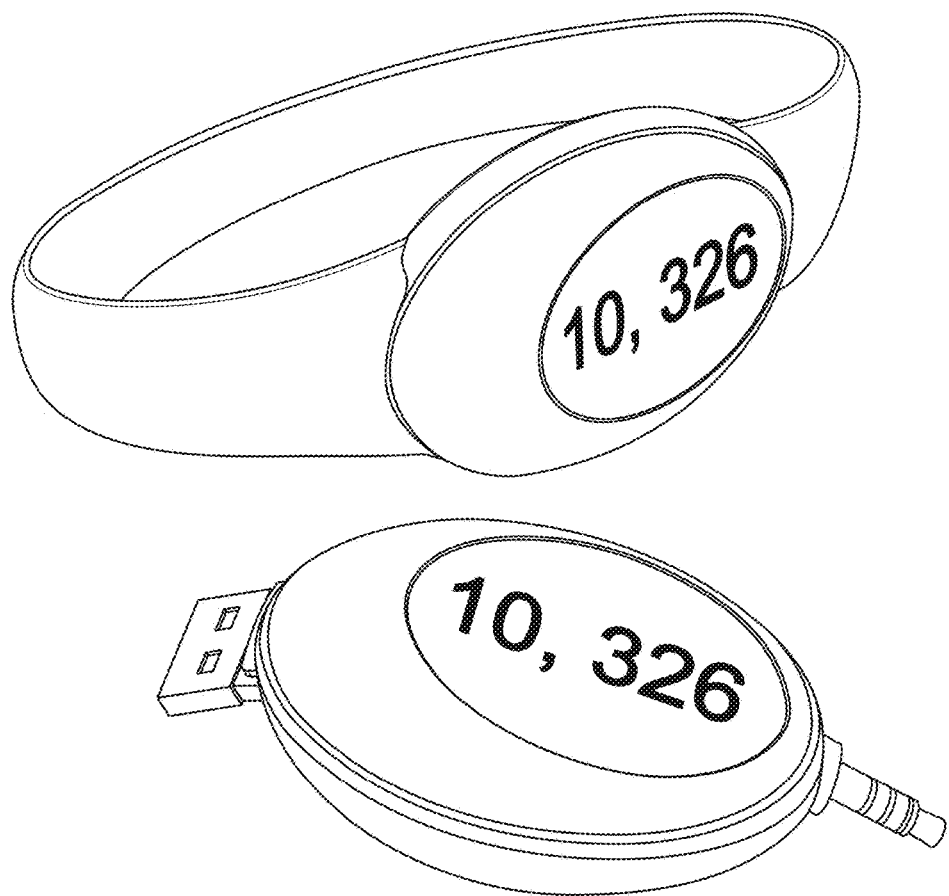
Figure 1D:
Figure 1E:
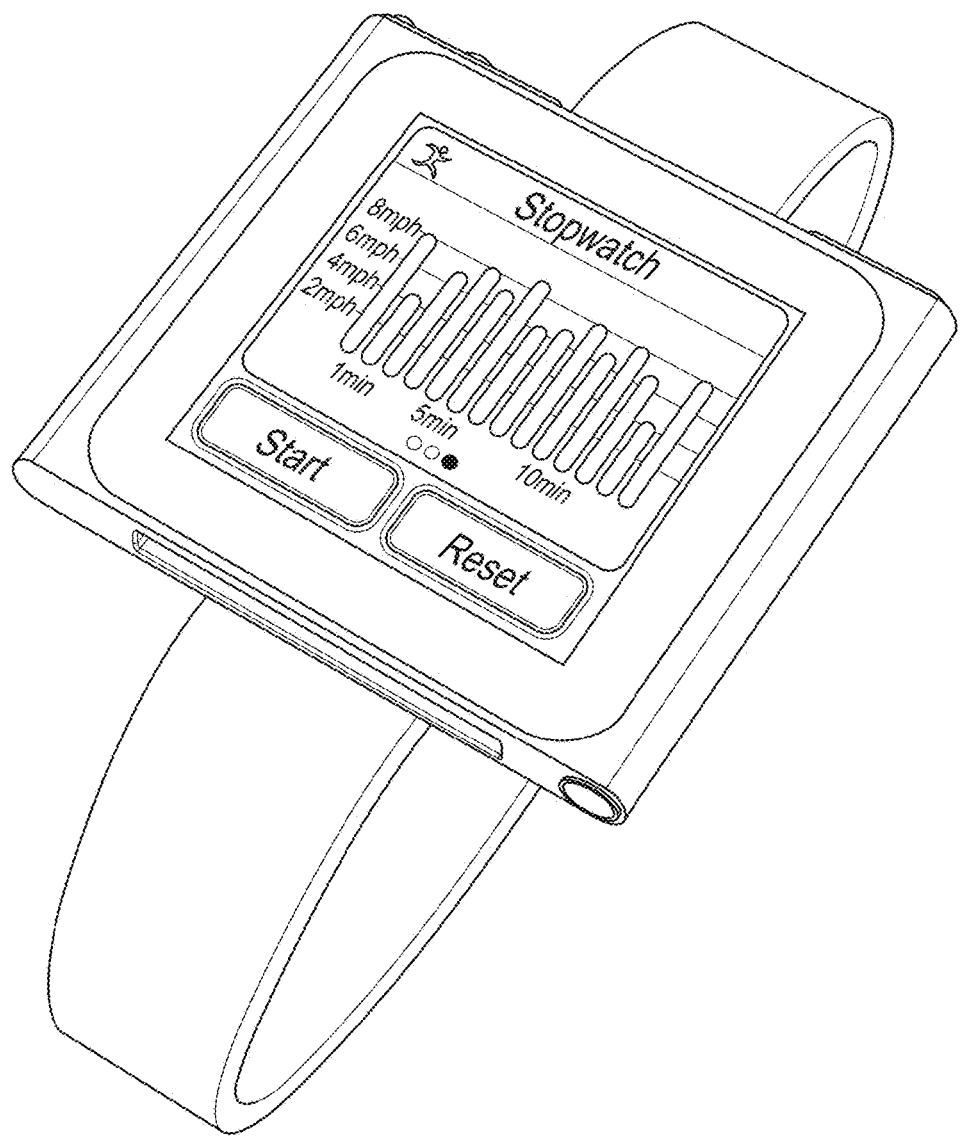

A system that enables user sleep monitoring is described. In one embodiment, the system enables the user to optimize their sleep patterns. For example, users can take power naps. Power naps are short naps, usually 20-35 minutes, which are of the right length to refresh, without taking too much time, and without making the user sluggish upon waking. In one embodiment, the system continually optimizes the length of a power nap for each individual based on analysis of previously obtained sleep and nap patterns and additional user information, when available. For a power nap, the monitor worn by the user determines when the user is falling asleep, and wakes the user at the calculated time interval automatically. In one embodiment, during a power nap, the system continues monitoring changes of sleep phases, and wakes up the subject before he or she crosses into non-REM sleep that would cause sluggishness.

In one embodiment, the sleep monitoring enables the timing of wake-up alarms for a longer sleep as well, such as a night's sleep. In one embodiment, the user defines a time window in which they want to wakeup. The device monitors sleep and finds the optimal time within that window to wake up the user. In one embodiment, that optimal time is when the user is transitioning from deep sleep to light sleep. In one embodiment, the user or the system specifies how many sleep cycles the user should sleep for. The system then wakes up the user after the specified number of sleep cycles.

In one embodiment, the number of sleep cycles may also be modified by a time window. The user can specify that they want to sleep for a number cycles, but they want to be woken up within a given time window no matter what. For example, the user may specify that they want to sleep for three sleep cycles, but wake up between 6 am and 8 am. If the user reaches the set number of sleep cycles before the time window, the system waits for another sleep cycle before sounding the alarm. If the sleep cycle count has not been reached by the end time of the alarm, the alarm will still go off within the time window.

In one embodiment, the monitor is implemented in a wristband. In one embodiment, the monitor may be implemented by small device designed to be worn on the body, on the wrist, arm, or elsewhere. In one embodiment, the implementation may be in an IPOD NANO® or similar small mobile device including sensors. Such a small mobile device may then be paired with an existing wristband, such as the band of a watch, bracelet, wristlet, wristband, etc. The small mobile device may similarly be attached to an armband, necklace, or other body-worn accessory. In another embodiment, the monitor may be implemented in a mobile device that is not worn on the body but placed on the sleeping surface, such as a bed. The user's movements may be monitored through the motions of the sleeping surface.

The following detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional and other changes may be made without departing from the scope of the present invention. The following detailed description is, therefore, not to be taken in a limiting sense, and the scope of the present invention is defined only by the appended claims.

Figure 1F:
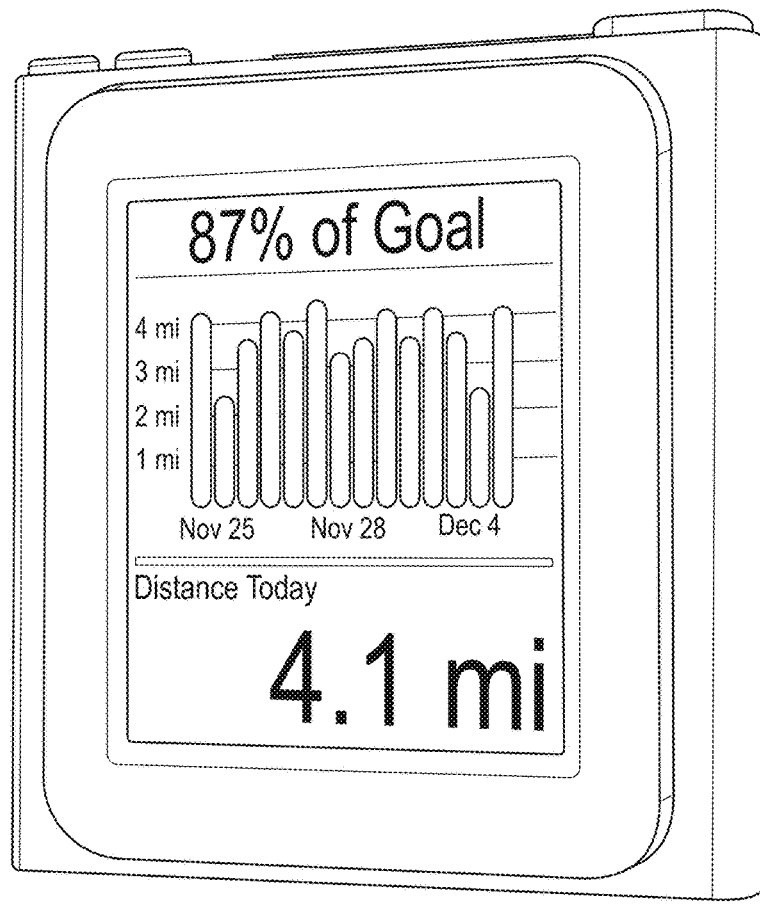

FIGS. 1A-1F are embodiments of the system. Various embodiments of a wristband or armband are shown. The embodiments include wristbands designed to be worn like a watch (FIGS. 1A, 1B, 1C, 1D), armbands (FIG. 1E), and devices that are designed to be attached to a bracelet or chest strap or similar body location (FIG. 1F). The system shown here may be used as an activity monitor and a sleep monitor. In one embodiment, the system is designed to be worn continuously, as described in co-pending application U.S. Ser. No. 12/819,195, filed Jun. 19, 2010, entitled "A Method and Apparatus to Provide Monitoring" which is incorporated herein by reference.

In one embodiment, the system may be a self-contained system, which includes a strap and the monitoring system. In another embodiment, the system may consist of a monitoring system that may be attached to an existing strap. For example, in one embodiment, the system may be implemented in a small mobile system such as an IPOD NANO™ that is designed to be attached to a wristband, bracelet, chest strap, or even pocket. In one embodiment, wristband/wrist watch/bracelet is preferred for measuring accuracy.

In one embodiment, the interface of the system may include one or more of: a full-sized USB connection (FIG. 1A), an audio jack connection (FIG. 1A), a micro-USB/mini-USB connection (FIG. 1C), a wireless connection which may be a cellular network connection or a WiFi connection (FIG. 1B), a dock connector (FIG. 1E), a proximity connection (FIG. 1D), or any other type of connection to enable the system to communicate with external devices. In one embodiment, those external devices may include a computer device, a server, one or more sensors, which may be coupled to the system, or other connections. In one embodiment, the processing described below may be partially performed by a server system 150 to which the sleep system is periodically coupled. This enables a low-processing power device to server as a motion sensor/sleep alarm.

Figure 1G:
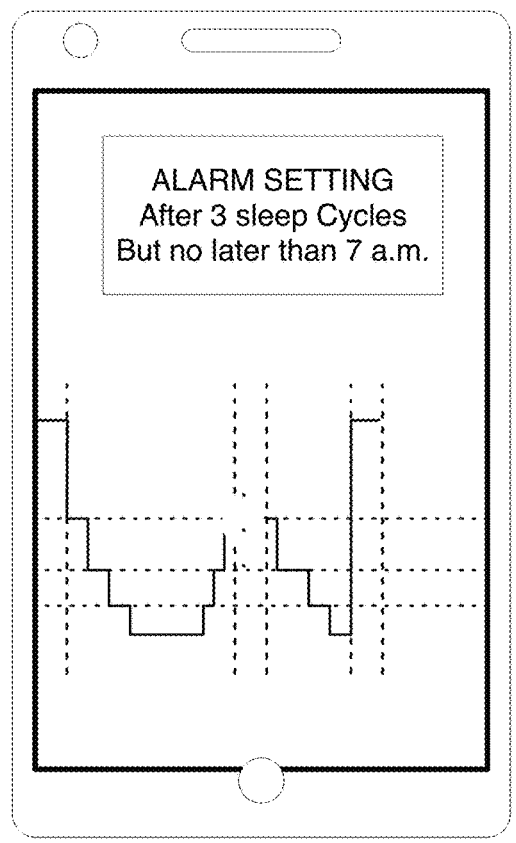

In one embodiment, the sleep system may be coupled to a mobile device, such as a smart phone, which provides processing. The smart phone, in turn, may be coupled to a server via a network. In one embodiment, the body-worn system is very simple, and only includes logic to provide user preference selection and timer. In another embodiment, the system may be a mobile device, as shown in FIG. 1G.

Figure 2:
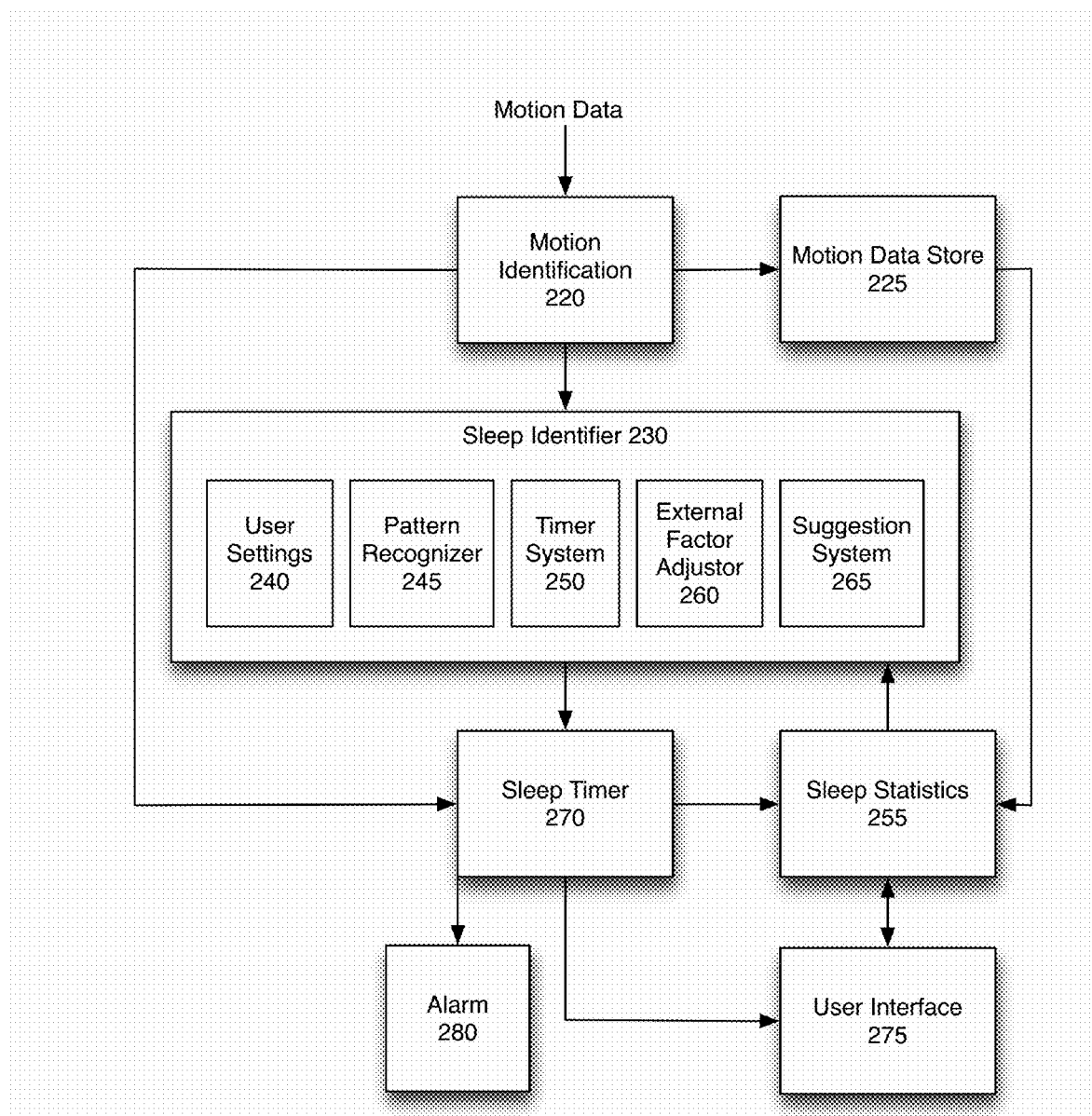
FIG. 2 is a block diagram of one embodiment of the monitoring system in accordance with the present invention.

FIG. 2 is a block diagram of one embodiment of the monitoring system in accordance with the present invention. In one embodiment, this system may be embodied within a body-worn device, designed to be worn by a user, in a mobile device, or another device including accelerometers and capable of monitoring a user's movements. In another embodiment, the function described may be split between a body-worn system, a mobile device, and a server. For example, the statistical calculations and/or user interface features may take place on a mobile device or a server. In another embodiment, the body-worn system works in conjunction with a server, without a mobile device. In another embodiment, the system may be embodied in a mobile device that is not worn by a user, but is a mobile device that may be placed in close proximity to the user.

A motion identification logic 220 receives motion data. Motion data may be received from an inertial sensor. In one embodiment, the inertial sensor may be one or more accelerometers, gyroscopes, or a combination of accelerometers and gyroscopes. Alternative systems, which provide motion data, now known or later discovered, may also be utilized.

Motion identification logic 220 uses the motion data to identify a user falling asleep, in one embodiment. The motions of wakefulness are different from the motions of sleep. The motion identification logic 220 identifies that the user has fallen asleep, in one embodiment. In one embodiment, the motion data is also sent to motion data store 225. In another embodiment, the motion identification logic 220 may be supplemented by or replaced with the user interface 275, allowing the user to indicate the initiation of a sleep session. In one embodiment, motion identification logic 220 can detect when the user is getting tired, and a power nap or longer sleep would be useful. In one embodiment, the system may suggest a power nap. In one embodiment, as a user is headed to sleep, the system suggests a sleep type, and a timing for waking up the user. The user can then adjust any of these settings or just keep the recommended settings. In one embodiment, some of these settings are fixed prior to going to sleep such as wake-up time range. In one embodiment, some settings are finalized after observing the user's sleep patterns. For example, the wake-up alert timing is dependent on actual measured sleep.

In one embodiment, sleep identifier 230 determines whether the user's sleep is a power nap, or another type of sleep. In one embodiment, power naps are taken generally during the day, during the late morning or early afternoon by most people. Sleep identifier 230 may rely on one or more of data from a user interface 275, pattern recognizer 245, sleep statistics 255, and timer system 250.

Figure 1H:
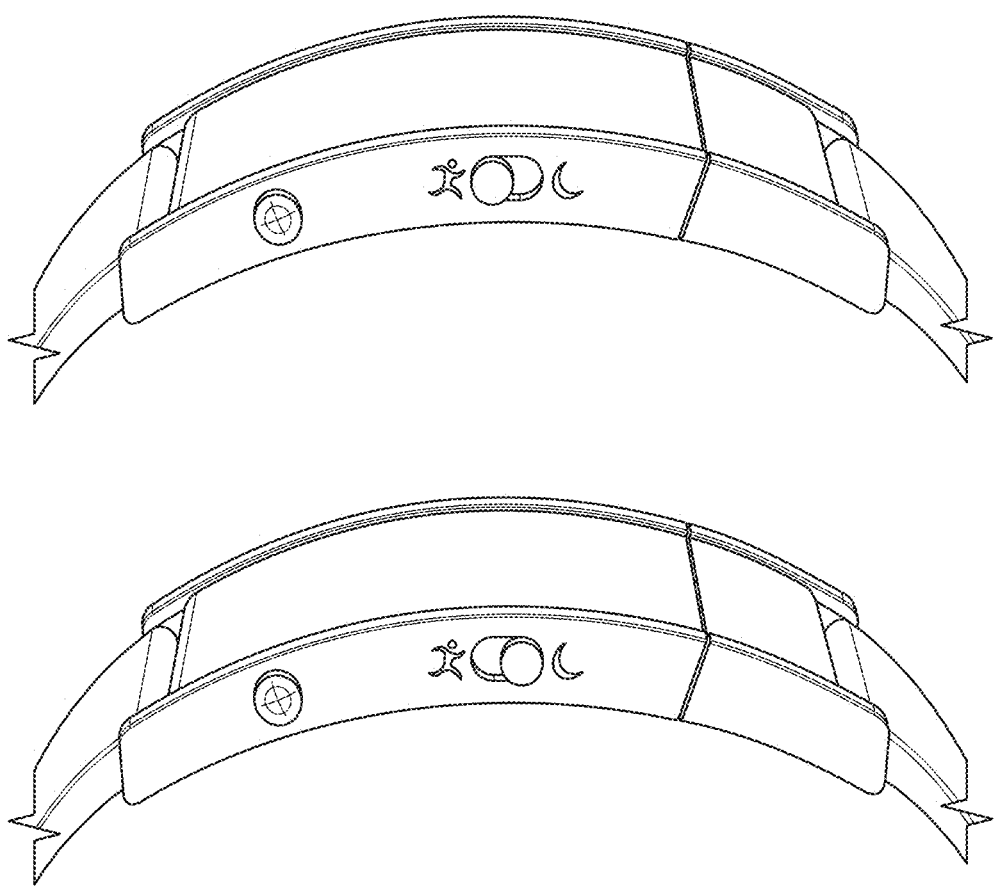
FIGS. 1H-1K are diagrams of embodiments of the user interface that may be used with the monitoring device.
Figure 1I:
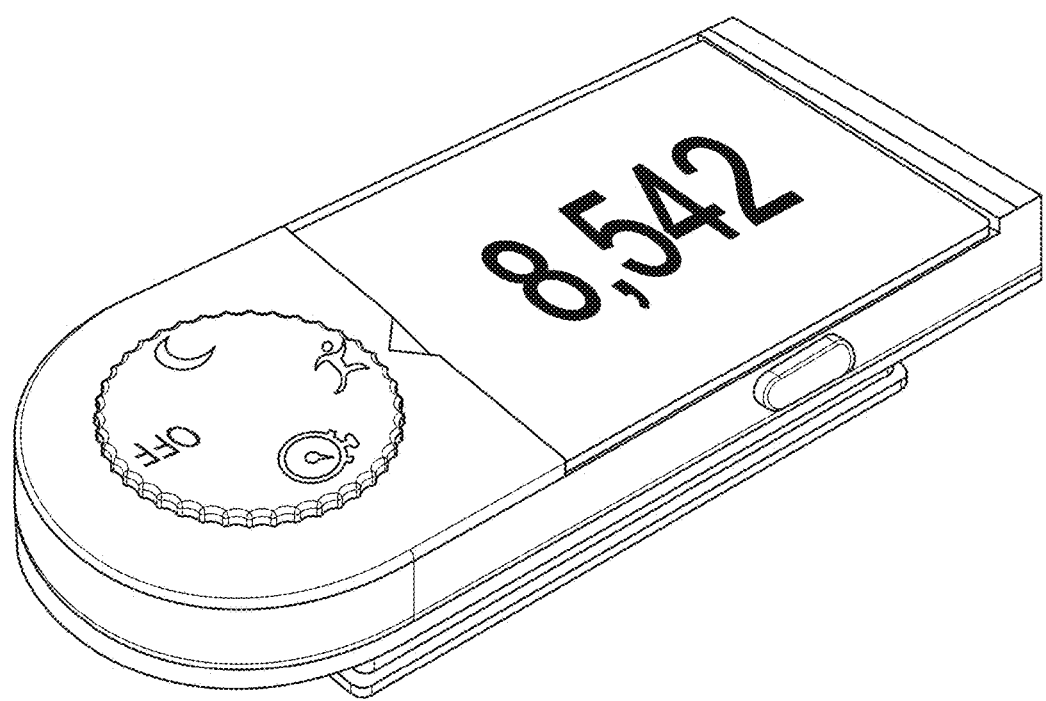
Figure 1J:
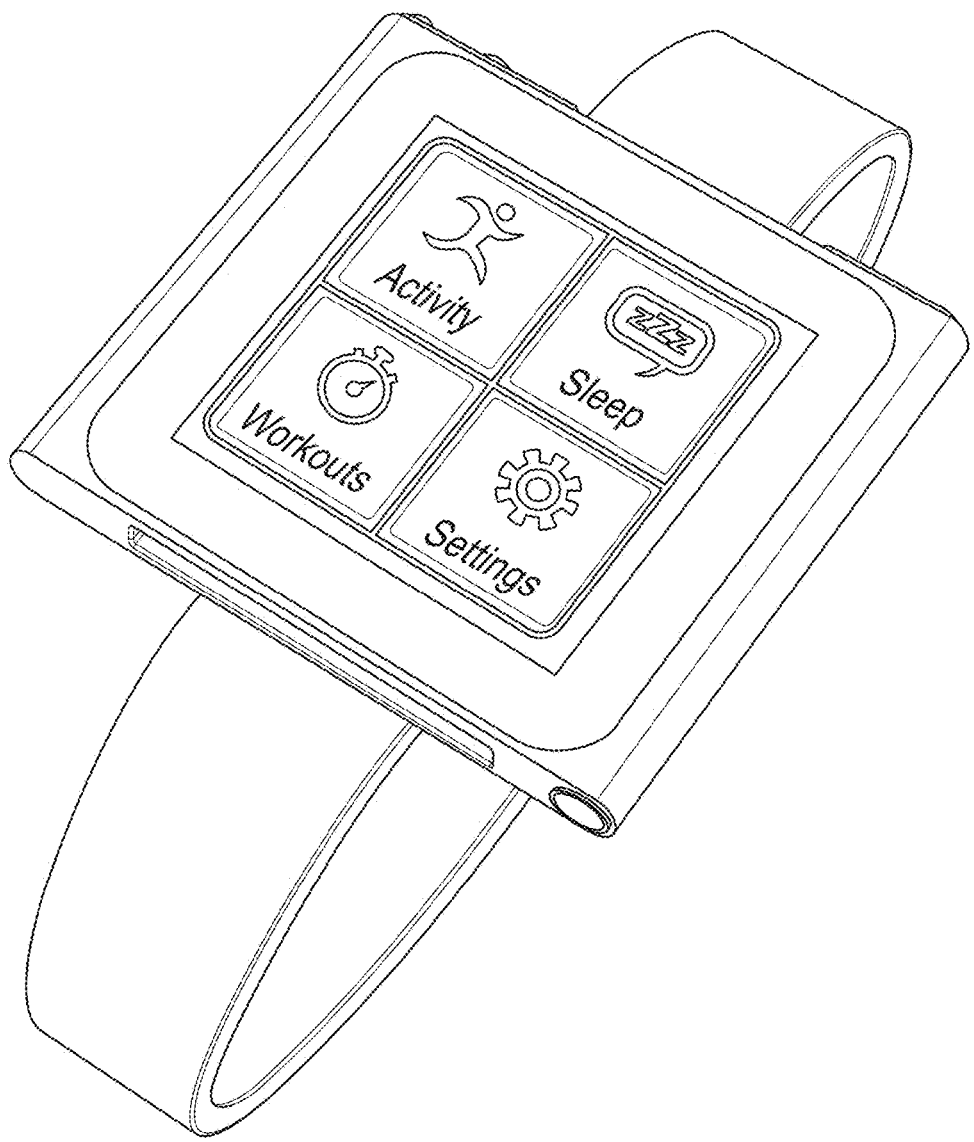
Figure 1K:
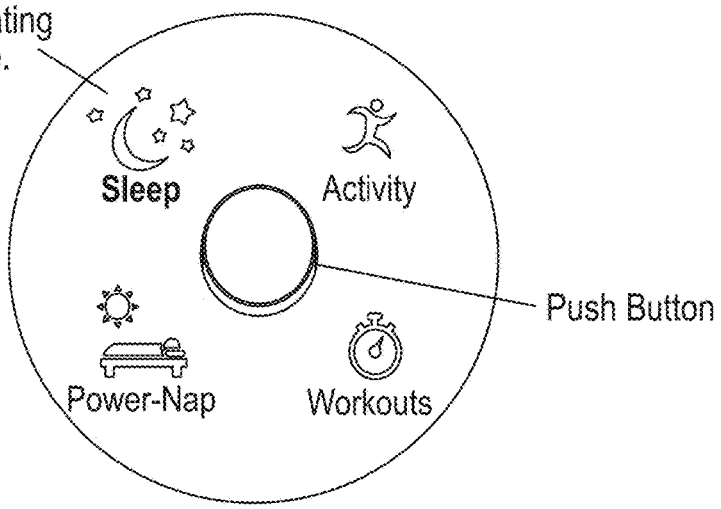
Figure 1K:

In one embodiment, user interface 275 enables a user to set the system to "power nap" state. As shown in FIG. 1H, the setting may be as simple as setting night or day, where daytime sleep is identified as a power nap. FIG. 1K shows a more detailed set of options, allowing a user to set sleep, activity, powernap, or workout. As noted above, in one embodiment, the motion sensing system may be used as an activity monitor in addition to a sleep monitor. That aspect of the system is not described in detail, as it is described in the above referenced co-pending application, which is incorporated by reference.

The user preference settings 240 may be used to identify sleep type, or an activation of a button may be used to indicate the initialization of a power nap.

In one embodiment, the sleep identifier 230 may use a pattern recognizer 245 to recognize that the sleep session should be identified as a power nap. The pattern recognizer uses the user's history of nap and sleep timing, to determine whether the current sleep should be classified as a power nap.

The sleep identifier 230 may also use a timer system 250 to determine whether the sleep session should be classified as a power nap. The timer system may determine the time since the user's last full sleep and/or the user's last power nap or standard nap to determine whether the current sleep should be a power nap or not. In general, a user would sleep overnight every 15-18 hours. Thus, a sleep less than 12 hours after the last full sleep cycle may be classified as a power nap. Timer system 250 may also use the current time of day to determine whether the sleep is a power nap. For example, most people take power naps between 1 p.m. and 4 p.m. Thus, if the user is sleeping during those times, it may be classified as a power nap. However, a user for example who is on the night shift and usually sleeps their longer sleep cycle between 8 a.m. and 4 p.m. would likely take a power nap at 1 a.m. or a similar time of day.

In one embodiment, external factor adjustor 260 may be used provide a suggestion to the user or may automatically set the sleep type, based on external factors. For example, if the user is headed to sleep and 2 p.m., and the user has a 3:00 p.m. meeting on their calendar, the suggestion system 265 suggests a 26.5 minute powernap (meaning 26.5 minutes of actual sleep) with a hard deadline of waking up the user at 2:45 p.m. so that the user will wake up in time for the meeting.

In one embodiment, the user may set preferences, including overriding the sleep identifier's identification. In one embodiment, the system has a rich user interface so user can double check the settings before falling asleep. For example, the system may provide a quiet indicator of the identified sleep type, enabling a user to override verbally, or through another user interface feature.

Of course, while these different aspects are described individually above, in one embodiment a combination of these methods may be used to accurately identify the sleep type. For example, the patterns may utilize the time of day and the time since the last sleep/nap, while the timer may utilize the sleep statistics 255 identifying the user's sleep pattern (e.g. someone on night shift has a different pattern than someone working the dayshift). In one embodiment, all of these settings are customized for the user over time. In on embodiment, the system is initially configured with default settings (e.g. sleep from 11 p.m. to 6 a.m., power nap from 2 p.m. to 2:30 p.m.), and the user may adjust these via a user interface. The system may further learn based on user input/experience. One embodiment, of the various power nap identifications are shown in FIG. 6.

When the power nap identifier identifies sleep as not being a power nap, the sleep alarm system timer 270 is consulted, if appropriate. If there is an alarm set, in one embodiment, it is timed so that the user wakes up in the appropriate sleep cycle. It is known that someone is more tired if he or she wakes up from a deeper sleep, compared to waking up at N1 or early N2 sleep.

The user may define a time window for waking up, using the user interface 275. The time window may, for example, state that the user wishes to wake up before 7:30 a.m. The motion identification logic 220 then uses the motion data, to determine the user's sleep cycle, and the alarm 280 wakes the user up at the optimal time. In one embodiment, that optimal time is when they are transitioning from deep sleep to light sleep.

In one embodiment, the user may define a number of sleep cycles he or she would like to sleep for, through the user interface 275. A sleep cycle is generally between 90 minutes (first sleep cycle) and 120 minutes (later sleep cycles). Therefore, the user may define a number of sleep cycles, to determine when to wake the user, with the alarm 280. In one embodiment, when the user defines the number of sleep cycles until the alarm, the system provides an estimated waking time to the user.

In one embodiment, the user may set a preferred number of sleep cycles, and add a time window mask so that the user can specify that they want to be woken up within a given time window no matter what. For example, the user may set four sleep cycles, but set that regardless of the number of sleep cycles, the user must be woken up between 6 am and 8 am. If the user reaches the set number of sleep cycles before the time window, the system waits for another sleep cycle before sounding the alarm. If the sleep cycle count has not been reached by the end time of the time window mask, the alarm will go off.

If sleep identifier 230 identifies the sleep session as a power nap, the sleep timer 270 is activated. The sleep timer 270 is designed to sound an alarm to wake the user after the optimal length power nap, e.g. when the user has received the benefit of the nap, but is likely to wake without grogginess. The sleep timer 270 uses user settings data for how/when to wake up. These user settings 240 include time window, number of sleep cycles, actually sleeping for a certain time, wake-up alert style (vibration, audio, what audio, how it ramps up, etc.). The user settings 240 can either be explicitly set by the user, auto set by the system based on user profile, habits, all other inputs such as calendar/schedule, or a mixture of auto-set and explicitly set user settings 240. Once the user settings 240 set the initial conditions, the measured details of the sleep session may include one or more of: time to fall asleep, sleep cycles, amount of light sleep and deep sleep, number and duration of awake events throughout the night, snoring, sleep talking and other noises monitored by the system. The sleep timer 240 uses these measured details, in conjunction with the user settings 240 to wake the user at the optimal time.

In one embodiment, the default power nap time is 26.5 minutes, which is the average optimal duration for adults. In one embodiment, the sleep timer 270 may be adjusted based on the historical sleep data collected for the particular user. In one embodiment, the optimal length is adjusted based on historical sleep data from the prior seven days. In another embodiment, the optimal length is adjusted based on historical sleep data from the prior month. In one embodiment, when the historical data extends beyond seven days, the last seven days are more heavily weighted in determining an optimal power nap time.

In one embodiment, at the first transition to N2, the deeper sleep phase, the user is wakened. In one embodiment, this is based on the sleep timer 270. In one embodiment, this may be based on a historical calculation of the length of an optimal power nap for this user. By using a simple timer, in one embodiment, it enables the more processor-intensive, and thus power-intensive, calculations of determining the sleep phase based on motion to be done separately from timing the power nap. In one embodiment, these calculations may be shifted off the sleep alarm system and to a more powerful device such as a smart phone, computer system, or server. In another embodiment, the timing may be determined based on the user's motion patterns, indicating the transition into N2.

Figure 7:
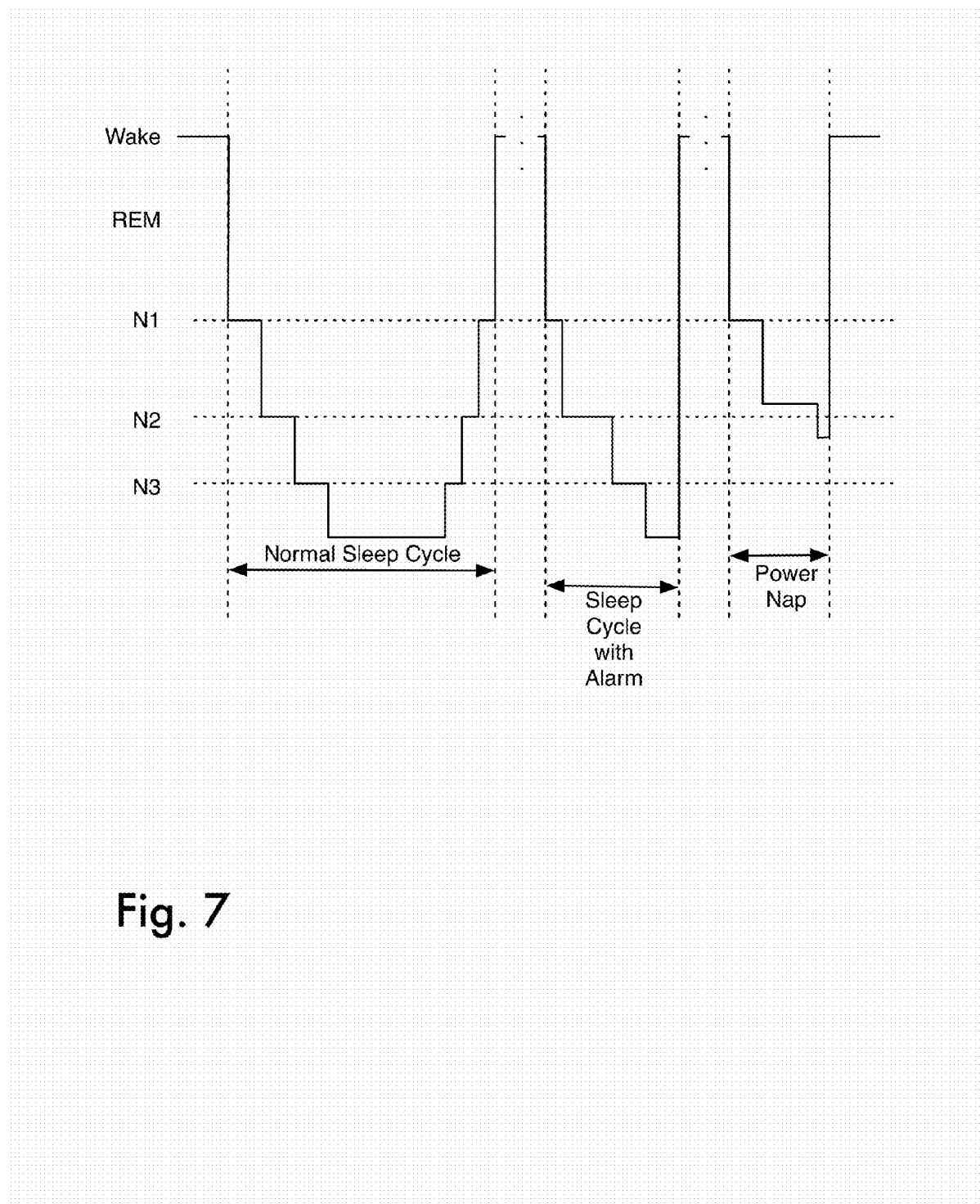
FIG. 7 is a hypnogram showing exemplary phases of sleep.

FIG. 7 is one embodiment of a hypnogram, explaining the various states of sleep. The first segment shows a normal short sleep cycle, with no waking and no alarm. As can be seen, the user starts awake, then goes into REM sleep, and then into N1, N2, and finally N3 stage of sleep. Generally, the later part of N2 and all of N3 are considered deep sleep.

The second segment shows an interrupted sleep cycle. The user gradually goes into deep sleep, and is yanked out of deep sleep when the alarm goes off, directly from N3 to awake. This would result in a groggy wakefulness, and an overall feeling that the sleep was not restful. Lastly, a power nap is shown. The power nap allows the user to go through REM, and N1, but just before the user starts drifting into N2, the alarm is sounded, and the user is awakened. Because the user is awakened before going into deep sleep, the sleep will be felt to be more refreshing and restful. Furthermore, the duration of the sleep and length of time needed is optimally balanced for feeling rested using the minimal amount of time.

For the alarm, described above, associated with a longer sleep, such as overnight, in one embodiment, the system times the waking to be at the N1 to N2 or N2 to N1 transition. This makes the transition to wakefulness smooth, and the sleep feel more restful.

Returning to FIG. 2, when the sleep timer 270 determines that it is time for the user to wake, it sends a signal to alarm 280. In one embodiment, the user may be wakened via an alarm, which may be visual, aural, or tactile. In one embodiment, since the system can detect when the user is awake, the alarm sounds until the user is awake. This enables even a loud alarm to sound for only a short time, until the user is awake.

The data about the sleep session is then sent to sleep statistics 255. Sleep statistics 255 tracks the data associated with each sleep session, in one embodiment. In one embodiment, sleep statistics 255 optionally also receives user input about the quality of the sleep. Sleep statistics 255 is used to continually optimize the length of a powernap, and the optimal length of a longer sleep, for each individual, in one embodiment. In one embodiment, this is based on rolling analysis of the last seven days of sleep data. In one embodiment, it is a longer period. In one embodiment, when a longer period than seven days is used, the last seven days of sleep are more heavily weighted. In one embodiment, the sleep statistics 255 identifies the outer limit of N1 on 7 days. The system then averages them and calculates a new power nap length that is optimal for the user. This enables the system to remain in sync with the user, even as the user's sleep patterns shift over time.

In one embodiment, after the user wakes from the sleep session, he or she may provide feedback about the sleep session, via user interface 275. The feedback may indicate that the sleep session was refreshing, that the user woke groggy, or that the user took a long time to wake between when the alarm sounded and when the user became active. In one embodiment, this last evaluation, e.g. the time between when the alarm sounds and the user becomes active, may be automatically detected and used to evaluate the quality of the sleep session. In one embodiment, this is used in the historical sleep data evaluation calculated by sleep statistics 255.

In one embodiment, movement patterns, from motion data store 225 are taken into account by sleep statistics 255 as well. In one embodiment, the sleep statistics 255 may correlate other factors with the quality of sleep of the user. For example, the system may correlate the user's activity level, or night-time sleep quality with the effectiveness of a power nap, and the timing of sleep sessions, including power naps and longer sleep.

In one embodiment, the sleep statistics 255 may further provide recommendations to the user, based on the statistical analysis. In one embodiment, these recommendations may be based on the sleep statistics and/or external data. In one embodiment, sleep statistics 255 receives other sleep information. For example, if a user has a bad night's sleep after a late, longer power nap, the system may adjust the recommended power nap length or timing.

Figure 3:
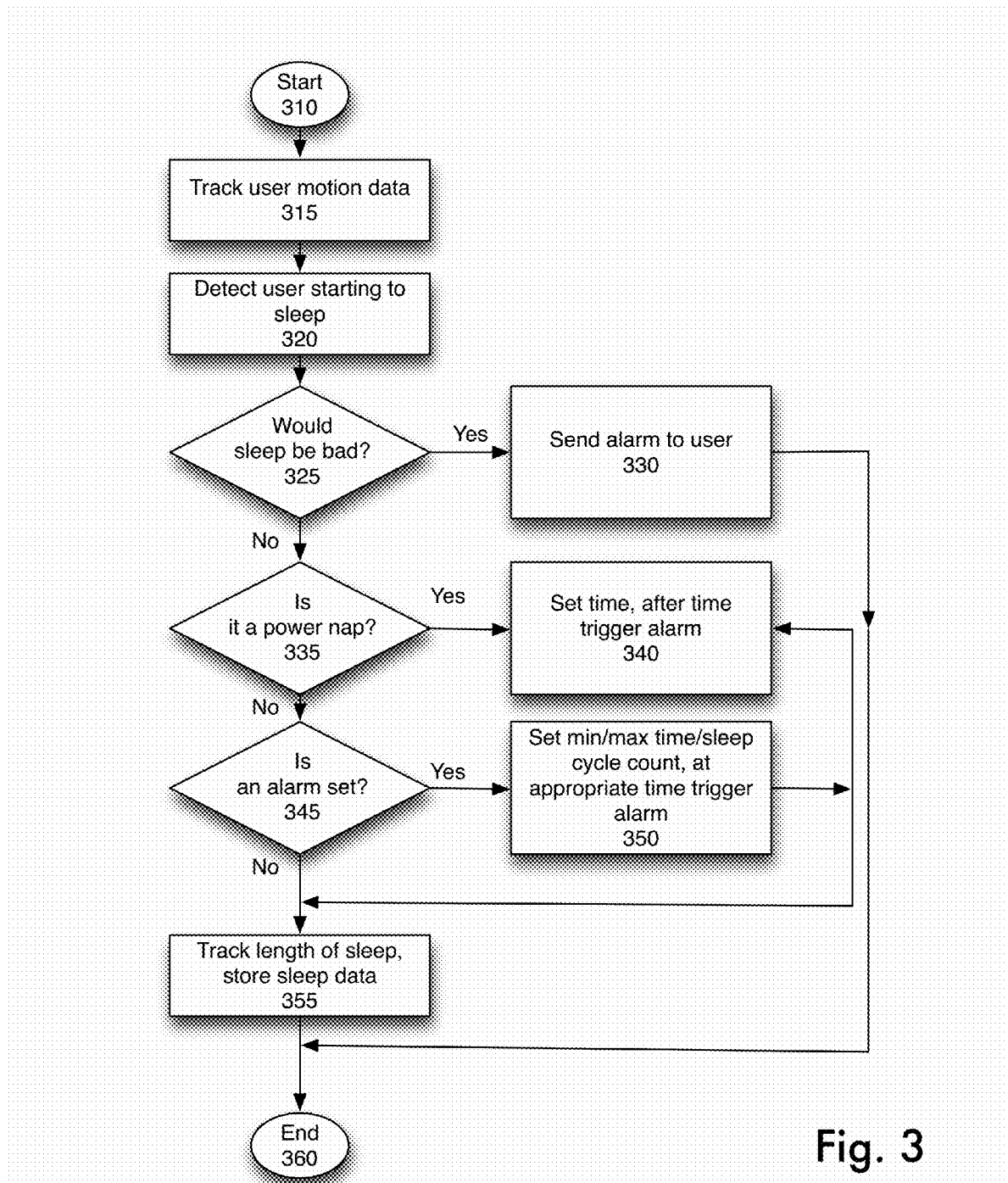
FIG. 3 is a flowchart of one embodiment of sleep alerts.

FIG. 3 is a flowchart of one embodiment of sleep alerts. The process start at block 310.

At block 315, the system tracks user motion data. This motion data may be used to track activity levels, eating patterns, and other aspects of the user's life. In one embodiment, the motion data is tracked using one or more accelerometers. In one embodiment, the accelerometers may be integrated into one or more devices. For example, a first accelerometer may be in a body-worn device such as a watch, bracelet, earphone, etc., while a second accelerometer is in a mobile device such as a smart phone, tablet computer, etc.

At block 320, the system detects that the user is starting to fall asleep. The characteristic body movement patterns associated with sleep are different than those associated with being awake. In another embodiment, the user may indicate that he or she is falling asleep through a user interface.

In embodiment, the system may determine whether sleeping would be a bad idea, at block 325. In one embodiment, this determination means a determination that the user can safely sleep, at block 325. In general, certain places are not safe for sleep, for example if the user is driving a vehicle or hiking at an elevation. In one embodiment, potential negative effects, in terms of health, sleep quality, quality of day may also be considered in determining whether sleep would be bad.

In one embodiment, if sleep would not be good, the system may send an alarm to the user, at block 330, to ensure that the user has a chance to move to a safe area for sleep. The process then ends at block 360. In one embodiment, the process continuously monitors the user's motion data (block 315) so the process continues to monitor even after the flowchart indicates that the process ends.

If it is safe to sleep, at block 335, the process determines whether the sleep just started is a power nap. In one embodiment, this determination is made based on time of day, time since last full sleep, and user input when available. If it is a power nap, at block 340 the system sets a timer, to wake the user up after the user's optimal power nap period. The process then continues to block 355, and the length of sleep is tracked. In one embodiment, the sleep data is also stored. In one embodiment, if user feedback is provided, it is associated with the sleep data. The sleep data may include movements during the sleep. As noted above, this may be added to cumulative statistics on the user's sleep experience. The process then ends at block 360.

If the sleep is not a power nap, the process continues to block 345. The system determines whether an alarm is set. As noted above, the alarm may be set with a time range, e.g. between 6 and 7 a.m., based on a number of sleep cycles, e.g. after three complete sleep cycles, or on a combination, e.g. after three complete sleep cycles, but no later than 7 a.m.

If an alarm is set, at block 350, the min/max time and/or sleep cycle count is set, based on the alarm setting. The system then triggers the alarm on the cycle point after the minimum time and prior to the maximum time, after the set number of sleep cycles, or prior to the maximum time. In one embodiment, when the min/max time is set, the system wakes the user as close to the max time as possible, while prioritizing waking the user in the correct sleep cycle.

In one embodiment, when the sleep cycle count, with a latest wake time window, is utilized, the system attempts to time the waking at a good time from a sleep phase perspective, but prior to the end of the wake time window. In one embodiment, this may lead to a wake time earlier than the end of the wake time window, without completion of the sleep cycle count.

In one embodiment, the user's sleep cycle is determined based on a default time, as adjusted by the user's historical data, as described in connection with the power nap above. In one embodiment, the user sets the alarm as a minimum length of sleep, and latest alarm (e.g. after 6 hours, but before 7 a.m.).

The process then continues to block 355, to store the length of sleep, and any available sleep data.

If there is no alarm, the system continues directly to block 355, to track the length of sleep, and store the sleep data. The stored sleep data, on power naps, sleep cycles with alarms, and sleep cycles without alarms is stored, and used by tracking system to determine optimal times for power naps. In one embodiment, the system may provide feedback about this data to the user. For example, the system may indicate to the user that when he or she takes a nap after 4:30 p.m. the night's sleep is less restful. This information may be useful to the user, in timing powernaps.

Figure 4:
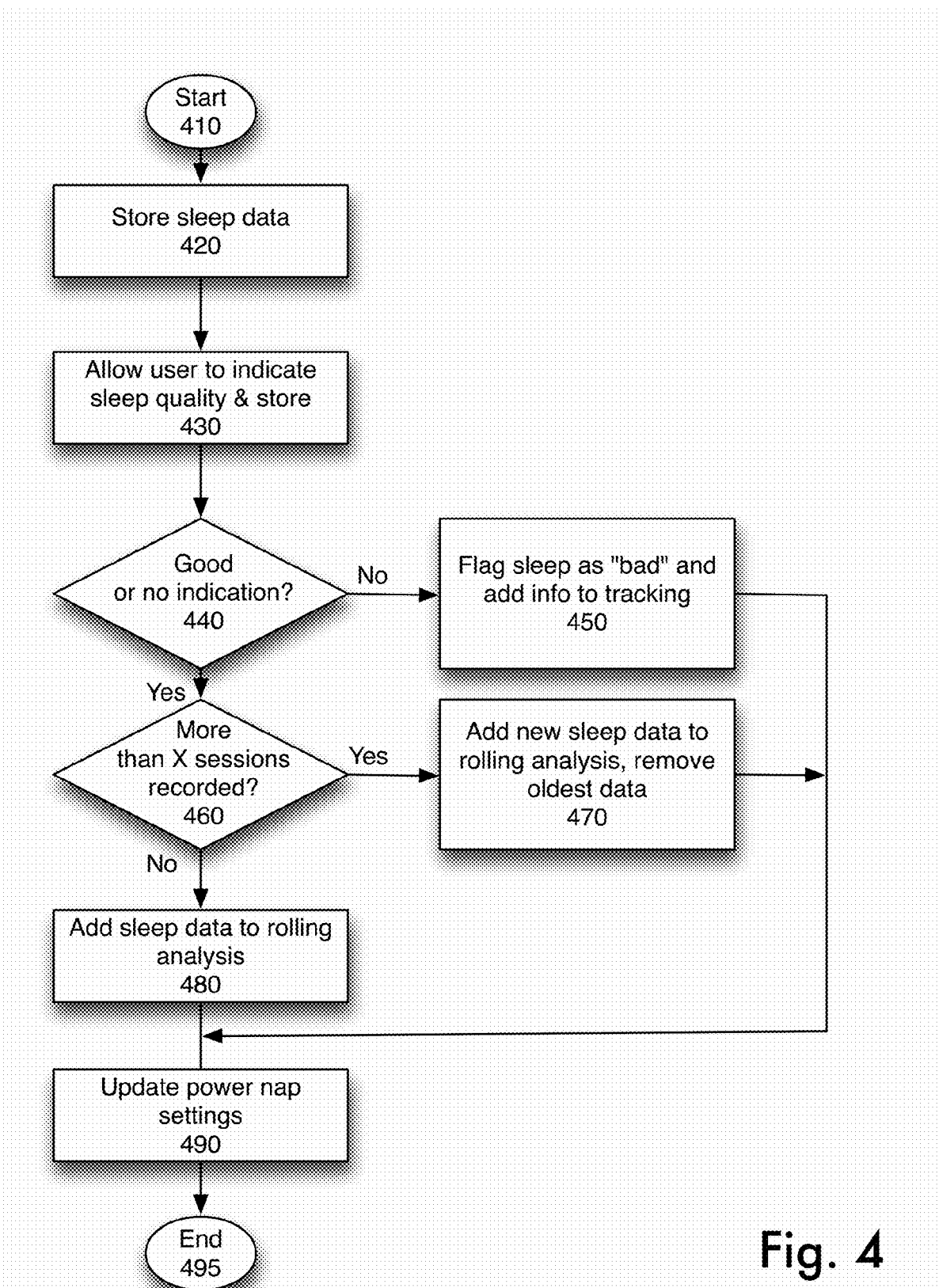
FIG. 4 is a flowchart of one embodiment of adjusting personal power nap settings.

FIG. 4 is a flowchart of one embodiment of adjusting personal power nap settings. The process starts at block 410. In one embodiment, this process may be run whenever a new powernap record is created. In one embodiment, this process may be run on a server, computer system, or mobile device. In another embodiment, this process may be run on the sleep sensing device. In another embodiment, it may be run periodically, based on various periods.

At block 420, the power nap data is stored.

At block 430, the user is able to indicate a nap quality. If any such indication is received, the user input is associated with the power nap record. In one embodiment, the user may indicate various moods, feelings, and states throughout the day. In one embodiment, the system may associate such data with the record of the day. This may be useful to track a user's overall state based on various factors including timing, quality, and quantity of sleep, power naps, etc.

At block 440, the process determines whether a particular power nap being evaluated is associated with a good indication, neutral indication, or no indication. If it is not, i.e. the indication is negative, the process at block 450 flags the nap as "bad" and adds this information to the tracking. In one embodiment, after a time, the system or the user can correlate the "bad" naps with certain events or timings that may have occurred. For example, the user may find that a nap too soon after a night's sleep is bad, or a nap shortly after eating is bad, etc. If the user suggests a correlation, this information is added to the system. If the system determines a correlation based on the data, this information is added to the system as well. The information is taken into account by the system in timing future naps. In one embodiment, the "bad to sleep" determination, discussed above with respect to FIG. 3, may take into account that the nap may have negative effects on the user's mood, ability to sleep at night, etc. If the probability that the nap will have a negative effect is above a threshold, the user may be warned with an alarm. If the user persists, in one embodiment, the user may override the alarm, and the system permits the user to sleep.

At block 490, the power nap settings are updated based on the additional data, if the additional data adds new information. In one embodiment, the power nap length is adjusted based on a seven day rolling average, or a weighted average of more days, with the last seven days more heavily weighted. The process then ends at block 495.

If there was no indication, or a positive or neural indication as determined at block 440, the process continues to block 460. At block 460, the process determines whether the system has information about more than the threshold number of naps. In one embodiment, the system keeps a rolling record of X naps, or X days of naps. In one embodiment, X may be 7.

If there have been more than X naps recorded, at block 470 the new nap data is added to the rolling analysis, and the oldest data is removed. If there haven't yet been X naps recorded, the process adds that data to the rolling analysis at block 480, but does not remove any data. In this way, the data is continually kept fresh. People's sleeping patterns change over time, and the use of the rolling averages for analysis keeps the system's information about the user in sync with the user's changing sleeping patterns over time.

At block 490, the power nap settings are updated, if appropriate. As noted above, the length of the "optimum" power nap is calculated and used by the system to set timing for waking up the user. This timing may be updated as new power nap information is received. The process then ends at block 495. In one embodiment, a similar process, not shown, is applicable to tracking longer sleep data as well. This analysis is used to update settings, and update recommendations provided to the user regarding sleep sessions. In one embodiment, other features, such as alarm type used, may also be adjusted based on the feedback received.

Figure 5:
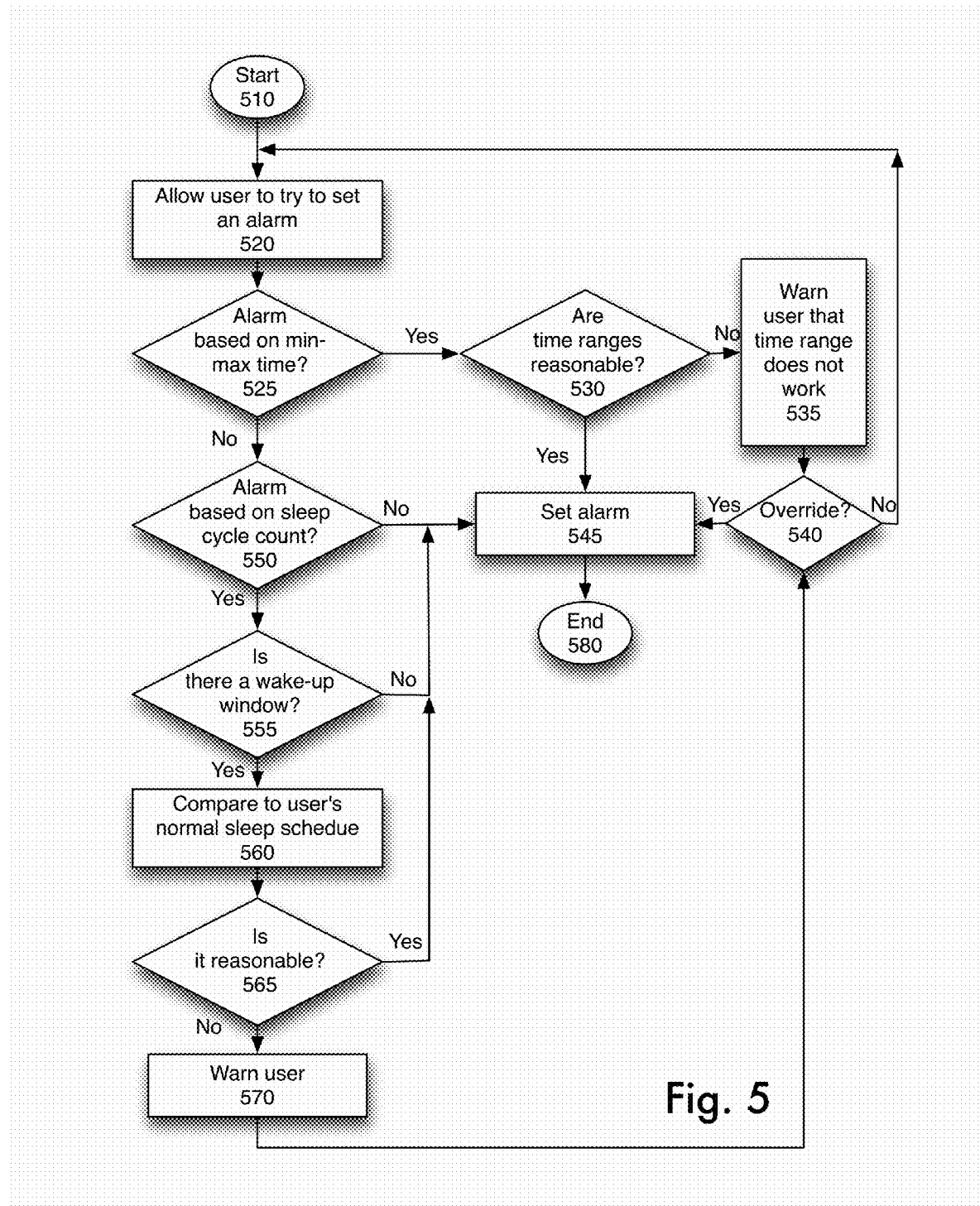
FIG. 5 is a flowchart of one embodiment of setting an alarm.

FIG. 5 is a flowchart of one embodiment of setting alarm settings, for longer sleep. Alarm settings, as noted above, may be based on a min/max time, a sleep cycle count, or a sleep cycle count in combination with a wake-up window. The process starts at block 510.

At block 520, the user attempts to set an alarm. In one embodiment, the user may be prompted to set a preferred alarm when he or she initially utilizes the system.

At block 525, the process determines whether the alarm the user set is based on min-max time. Min-max time sets the earliest and latest wake-up times. For example, the user may indicate he or she wishes to wake up between 6 a.m. and 7 a.m., at the best possible sleep phase within that time range.

If the user is setting min/max time, at block 530 the process determines whether the time range suggested is reasonable. In general, an entire sleep cycle is 90 minutes, and of that the average sleeper spends approximately 45 to 65 minutes in deep sleep. Therefore, setting a min-max that is only a short time apart may not be reasonable. If the timing is reasonable, at block 545 the alarm is set, and the process ends at block 580.

If the time range was found to be unreasonable, at block 535 the user is warned. The user can optionally override the warning, and set the alarm anyway. If that is the user's choice, as determined at block 540, the alarm is set at block 545. If the user does not override the warning, the process returns to block 520, to allow the user to set the alarm.

If, at block 525, the process determined that the alarm was not based on min-max, the process continues to block 550. At block 550, the process determines whether the alarm is set based on sleep cycle count. If the alarm is not set based on sleep cycle count, at block 545, the alarm is set.

If the alarm is based on a sleep cycle count, at block 555 the process determines whether there is a wake-up window associated with the alarm. If there is no wake-up window, the process sets the alarm, at block 545.

If the user's alarm defined a sleep cycle count in combination with a wakeup window, the process continues to block 560.

At block 560, the process compares the proposed alarm to the user's normal schedule. In one embodiment, if schedule information is not yet available, this step may be skipped. The comparison is to determine whether the proposed alarm set-up is compatible with the user's schedule.

In one embodiment, the compatibility utilizes the current time, as well as settings to determine whether the proposed alarm would work. The system verifies that the user's preferences are realistic. For example, if the user indicates that he or she wishes to sleep for four full sleep cycles, and wake up in five hours, the system would indicate to the user that this preference is not likely to be achieved. The average length of a full sleep cycle is between 90 minutes and 120 minutes, for most people. In one embodiment, the realism of the user's sleep cycle/wake window preferences is compared to a default sleep cycle. In one embodiment, the user's own sleep cycle data is used to evaluate the user's preference. If it is not reasonable, the system warns the user at block 570. In one embodiment, the system may inform the user of the mismatch between the user's sleep cycle length, sleep timing, and wake up window. The user may override the warning, at block 540 to set the alarm, or may alter the settings.

In one embodiment, the reasonableness determination, at block 565, examines the user's historical patterns of sleep. If there is a mismatch between the alarm preferences and the actual sleep patterns of the user, the system may alert the user. For example, if a user consistently goes to bed at 2 a.m., but sets an alarm preference of four sleep cycles, and a latest waking of 7 a.m., the system may suggest that this set of preferences is not compatible with the known sleeping pattern of the user. If it is not reasonable, the system warns the user, at block 570. If the timing is found to be reasonable, the process sets the alarm at block 545, and ends at block 580.

Figure 8:
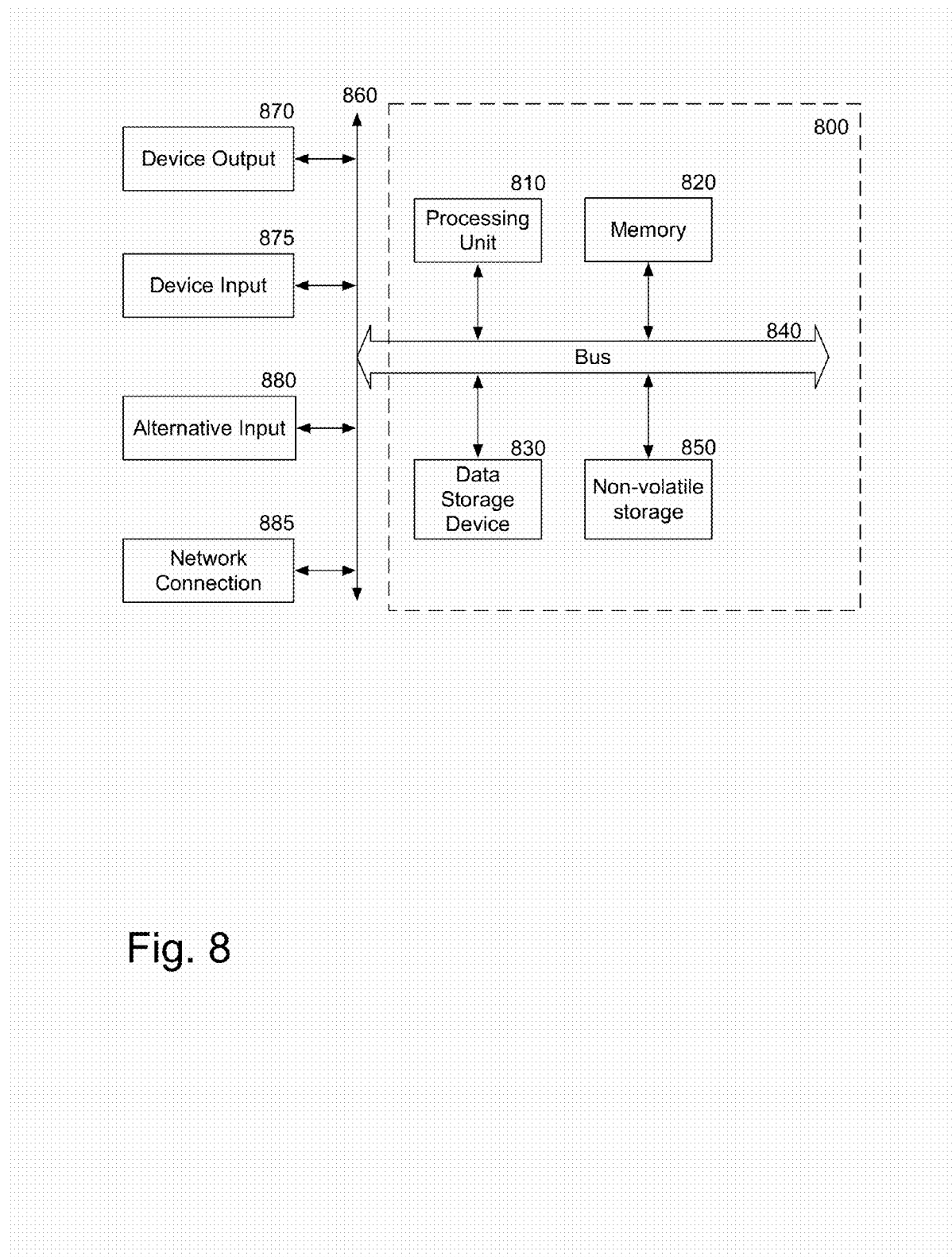
FIG. 8 is a block diagram of a computer system that may be used with the present invention.

FIG. 8 is a block diagram of a particular machine, which may be used with the present invention. It will be apparent to those of ordinary skill in the art, however that other alternative systems of various system architectures may also be used.

The data processing system illustrated in FIG. 8 includes a bus or other internal communication means 840 for communicating information, and a processing unit 810 coupled to the bus 840 for processing information. The processing unit 810 may be a central processing unit (CPU), a digital signal processor (DSP), or another type of processing unit 810.

The system further includes, in one embodiment, a random access memory (RAM) or other volatile storage device 820 (referred to as memory), coupled to bus 840 for storing information and instructions to be executed by processor 810. Main memory 820 may also be used for storing temporary variables or other intermediate information during execution of instructions by processing unit 810.

The system also comprises in one embodiment a read only memory (ROM) 850 and/or static storage device 850 coupled to bus 840 for storing static information and instructions for processor 810. In one embodiment the system also includes a data storage device 830 such as a magnetic disk or optical disk and its corresponding disk drive, or Flash memory or other storage which is capable of storing data when no power is supplied to the system. Data storage device 830 in one embodiment is coupled to bus 840 for storing information and instructions.

The system may further be coupled to an output device 870, such as a cathode ray tube (CRT) or a liquid crystal display (LCD) coupled to bus 840 through bus 860 for outputting information. The output device 870 may be a visual output device, an audio output device, and/or tactile output device (e.g. vibrations, etc.)

An input device 875 may be coupled to the bus 860. The input device 875 may be an alphanumeric input device, such as a keyboard including alphanumeric and other keys, for enabling a user to communicate information and command selections to processing unit 810. An additional user input device 880 may further be included. One such user input device 880 is cursor control device 880, such as a mouse, a trackball, stylus, cursor direction keys, or touch screen, may be coupled to bus 840 through bus 860 for communicating direction information and command selections to processing unit 810, and for controlling movement on display device 870.

Another device, which may optionally be coupled to computer system 800, is a network device 885 for accessing other nodes of a distributed system via a network. The communication device 885 may include any of a number of commercially available networking peripheral devices such as those used for coupling to an Ethernet, token ring, Internet, or wide area network, personal area network, wireless network or other method of accessing other devices. The communication device 885 may further be a null-modem connection, or any other mechanism that provides connectivity between the computer system 800 and the outside world.

Note that any or all of the components of this system illustrated in FIG. 8 and associated hardware may be used in various embodiments of the present invention.

It will be appreciated by those of ordinary skill in the art that the particular machine which embodies the present invention may be configured in various ways according to the particular implementation. The control logic or software implementing the present invention can be stored in main memory 820, mass storage device 830, or other storage medium locally or remotely accessible to processor 810.

It will be apparent to those of ordinary skill in the art that the system, method, and process described herein can be implemented as software stored in main memory 820 or read only memory 850 and executed by processor 810. This control logic or software may also be resident on an article of manufacture comprising a computer readable medium having computer readable program code embodied therein and being readable by the mass storage device 830 and for causing the processor 810 to operate in accordance with the methods and teachings herein.

The present invention may also be embodied in a handheld or portable device containing a subset of the computer hardware components described above. For example, the handheld device may be configured to contain only the bus 815, the processor 810, and memory 850 and/or 825.

The handheld device may be configured to include a set of buttons or input signaling components with which a user may select from a set of available options. These could be considered input device #1 875 or input device #2 880. The handheld device may also be configured to include an output device 870 such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above. For example, the appliance may include a processing unit 810, a data storage device 830, a bus 840, and memory 820, and no input/output mechanisms, or only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism. In one embodiment, the device may not provide any direct input/output signals, but may be configured and accessed through a website or other network-based connection through network device 885.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 810. A machine-readable medium includes any mechanism for storing information in a form readable by a machine (e.g. a computer). For example, a machine-readable medium includes read-only memory (ROM), random access memory (RAM), magnetic disk storage media, optical storage media, flash memory devices, or other storage media which may be used for temporary or permanent data storage. In one embodiment, the control logic may be implemented as transmittable data, such as electrical, optical, acoustical or other forms of propagated signals (e.g. carrier waves, infrared signals, digital signals, etc.)

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A computer-implemented method for monitoring sleep comprising:
   receiving data from an accelerometer worn by a user;
   analyzing by a processor the data from the accelerometer to determine that the user has fallen sleep;
   upon determining that the user has fallen asleep, determining automatically by the processor whether a current sleep episode is a power nap or a long sleep, based on a sleep time data, the sleep time data comprising a combination of: a duration since a last long sleep, a time of day, any upcoming appointment, and a history of timing of at least one of: a previous power nap and a previous long sleep;
   learning by the processor to accurately identify, using a rolling analysis of the sleep time data the sleep episode and keeping the processor's identifying of the sleep episode in sync with the user's changing sleeping patterns over time;
   wherein when the sleep episode is determined by the processor to be a power nap, the processor triggering an alert at a time prior to the user going into a deep sleep, the time being determined by the processor based on a statistical analysis of a length of the user's sleep cycle and an optimal sleep length for the user during the power nap; and
   wherein when the sleep episode is determined by the processor to be a long sleep, and the processor includes a user preference for a waking time, sending by an alarm an alert based on the user preference for the waking time, at an optimal point in the user's sleep cycle.

2. The method of claim 1, further comprising:
   receiving, by the processor, a command entered by the user prior to falling asleep to override the automatic determination that the sleep episode is a power nap or a long sleep, the command entered using one of: a user interface dial, a user interface button, or a menu.

3. The method of claim 1, wherein the accelerometer is located in a wristband.

4. The method of claim 1, further comprising:
   providing, by the processor, the accelerometer data to a server.

5. The method of claim 1, wherein the statistical analysis further comprises adjusting a default optimum time for a power nap based on historical sleep data from the user.

6. The method of claim 1, further comprising:
   when the long sleep is identified by the processor, determining whether an alarm is set by the user, the alarm set being based on one of: a minimum or maximum time, a number of sleep cycles completed, or a number of sleep cycles completed within a maximum time window.

7. The method of claim 6, wherein when the alarm is set by the user based on the minimum or maximum time, the user is woken up at an optimal sleep cycle time, at a latest point in the minimum or maximum time.

8. The method of claim 6, wherein when the alarm is set by the user based on the number of sleep cycles completed within a maximum time window, further comprising:
   attempting, by the processor, to wake the user at an optimal time, when the maximum time window expires prior to the completion of the number of sleep cycles set in the alarm.

9. A system for monitoring sleep comprising:
   a sensor designed to be worn by a user, to generate sensor data;
   a processor configured to analyze the sensor data from the sensor to determine that the user is asleep,
   the processor being configured to automatically determine, while the user is asleep, whether a current sleep episode is a power nap or a long sleep based on sleep time data, the sleep time data comprising a combination of: a duration since a last long sleep, a time of day, and a history of timing of at least one of: a previous power nap and a previous long sleep;
   wherein the processor further learns to accurately identify the sleep episode, based on a rolling analysis of the sleep time data, and the rolling analysis of the sleep time data enables the processor's identifying of the sleep episode to remain in sync with the user's changing sleeping patterns over time;
   the processor being configured to trigger an alert at a time prior to the user going into a deep sleep based on a statistical analysis of a length of the user's sleep cycle and an optimal sleep length for the user;
   wherein when the processor includes a user preference for a waking time, the processor further being configured to trigger the an-alert based on the user preference for the waking time, at an optimal point in the user's sleep cycle;
   wherein when the processor includes no user preference for the waking time, the processor further being configured to automatically select a waking time, and to trigger the alert based on the automatically selected waking time, at an optimal point in the user's sleep cycle; and,
   an alarm configured to communicate the alert.

10. The system of claim 9, further comprising:
    a user interface configured to receive a command entered by the user prior to falling asleep to override the determination of whether the sleep episode is the power nap or the long sleep, the user interface comprising one of: a user interface dial, a user interface button, or a menu.

11. The system of claim 9, wherein the sensor is an accelerometer located in a wristband.

12. The system of claim 9, further comprising:
    a server configured to receive the sensor data; and
    a user interface configured to make the sensor data available to the user.

13. The system of claim 9, wherein the statistical analysis further comprises adjusting a default optimum time for a power nap based on historical sleep data from the user.

14. The system of claim 9, further comprising:
    a sleep timer configured to determine whether the alarm is set by the user when the long sleep is identified by the processor, the alarm being set based on one of: a minimum or maximum time, a number of sleep cycles completed, or a number of sleep cycles completed within a maximum time window.

15. The system of claim 14, wherein when the alarm is set by the user based on the minimum or maximum time, the alert is sent at an optimal sleep cycle time, at a latest point in the minimum or maximum time.

16. The system of claim 14, wherein when the alarm is set by the user based on the number of sleep cycles completed within a maximum time window, further comprising:

the alarm configured to send the alert at an optimal time, when the maximum time window expires prior to the completion of the number of sleep cycles set in the alarm.

17. A system for monitoring sleep comprising:

a sensor designed to be worn by a user, to generate sensor data;

a processor configured to analyze the sensor data from the sensor to determine that the user has fallen to asleep;

the processor being configured to automatically determine, while the user is asleep, whether a current sleep episode is a power nap or a long sleep based on sleep time data, the sleep time data comprising a combination of: a duration since a last long sleep, a time of day, and a history of timing of at least one of: a previous power nap and a previous long sleep;

the processor further being configured to trigger an alert to wake the user, wherein when the current sleep episode is a power nap, the processor triggers the alert at a time prior to the user going into a first deep sleep, and when the current sleep episode is a long sleep, the processor triggers the alert based on the user preference for a waking time, at an optimal point in the user's sleep cycle; and, an alarm configured to communicate the alert.

* * * * *